(12) United States Patent
Ravuna et al.

(10) Patent No.: US 9,949,657 B2
(45) Date of Patent: Apr. 24, 2018

(54) DISPLAYING MULTIPLE-ACTIVATION AREAS ON AN ELECTROANATOMICAL MAP

(71) Applicant: BIOSENSE WEBSTER (ISRAEL) LTD., Yokneam (IL)

(72) Inventors: Eliyahu Ravuna, Kiryat Ata (IL); Lior Botzer, Timrat (IL)

(73) Assignee: Biosense Webster (Israel) Ltd. (IL)

(*) Notice: Subject to any disclaimer, the term of this patent is extended or adjusted under 35 U.S.C. 154(b) by 141 days.

(21) Appl. No.: 14/960,904

(22) Filed: Dec. 7, 2015

(65) Prior Publication Data

US 2017/0156613 A1 Jun. 8, 2017

(51) Int. Cl.
| | |
|---|---|
| *A61B 5/044* | (2006.01) |
| *G06F 3/0484* | (2013.01) |
| *G09G 5/06* | (2006.01) |
| *G09G 5/02* | (2006.01) |
| *A61B 5/04* | (2006.01) |
| *A61B 5/042* | (2006.01) |
| *A61B 5/00* | (2006.01) |
| *A61B 5/0456* | (2006.01) |
| *A61B 5/046* | (2006.01) |
| *A61B 5/0464* | (2006.01) |

(52) U.S. Cl.
CPC ............ *A61B 5/044* (2013.01); *A61B 5/042* (2013.01); *A61B 5/04012* (2013.01); *A61B 5/0456* (2013.01); *A61B 5/6852* (2013.01); *A61B 5/743* (2013.01); *G06F 3/04847* (2013.01); *G09G 5/026* (2013.01); *G09G 5/06* (2013.01); *A61B 5/046* (2013.01); *A61B 5/0464* (2013.01); *G09G 2320/0666* (2013.01); *G09G 2340/14* (2013.01); *G09G 2354/00* (2013.01); *G09G 2380/08* (2013.01)

(58) Field of Classification Search
CPC ....... A61B 5/044; A61B 5/743; A61B 5/0456; A61B 5/04012; A61B 5/0468
See application file for complete search history.

(56) References Cited

U.S. PATENT DOCUMENTS

| | | | |
|---|---|---|---|
| 6,226,542 B1 | 5/2001 | Reisfeld | |
| 6,301,496 B1 | 10/2001 | Reisfeld | |
| 6,892,091 B1 | 5/2005 | Ben-Haim et al. | |

(Continued)

FOREIGN PATENT DOCUMENTS

WO    WO 2010/054409 A1    5/2010

OTHER PUBLICATIONS

European Search Report dated Apr. 3, 2017 from corresponding European Patent Application No. 16202441.8.

(Continued)

*Primary Examiner* — George Evanisko
(74) *Attorney, Agent, or Firm* — Vincent J. Serrao (57) ABSTRACT

A method for displaying electroanatomical information is provided. The method comprises identifying at least one multiple-activation area of a surface of a heart, at which multiple-activation area were recorded at least two different local activations during a single cardiac cycle of the heart. The multiple-activation area is displayed, on an electroanatomical map of the surface of the heart, in a manner that indicates a time difference between respective times of the two local activations. Other embodiments are also described.

21 Claims, 3 Drawing Sheets

(56) References Cited

U.S. PATENT DOCUMENTS

| | | |
|---|---|---|
| 2007/0299351 A1 | 12/2007 | Harlev et al. |
| 2010/0094274 A1 | 4/2010 | Narayan et al. |
| 2012/0184863 A1* | 7/2012 | Harlev .................. G06F 19/322 600/509 |
| 2013/0109945 A1 | 5/2013 | Harlev et al. |
| 2014/0336520 A1 | 11/2014 | Zeng et al. |
| 2015/0119735 A1 | 4/2015 | Yang et al. |

OTHER PUBLICATIONS

Roux, Jean-Francois, M.D. et al., "Complex Fractionated Electrogram Distribution and Temporal Stability in Patients Undergoing Atrial Fibrillation Ablation", Journal of Cardiovascular Electrophysiology, Aug. 1, 2008, pp. 815-820, vol. 19, No. 8.

Nakagawa et al., "Rapid High Resolution Electroanatomical Mapping", Circulation: Arrhythmia and Electrophysiology, 2012; vol. 5, Issue 2, pp. 417-424.

ISSA, Ziad F. et al., "Clinical Arrhythmology and Electrophysiology: A Companion to Braunwald's Heart Disease", Philadelphia, PA, Elseiver/Saunders, p. 257, 2012.

\* cited by examiner

DISPLAYING MULTIPLE-ACTIVATION AREAS ON AN ELECTROANATOMICAL MAP

FIELD OF THE INVENTION

The present invention relates to the field of electroanatomical mapping, specifically of the heart.

BACKGROUND

A "local activation time" of a particular area of the heart is the time at which the wavefront of electrical propagation passes through the area. A local activation time is typically measured from a particular reference time, such as a particular point in time in the QRS complex of a body-surface electrocardiogram (ECG) recording.

Nakagawa et al., "Rapid High Resolution Electroanatomical Mapping," Circulation: Arrhythmia and Electrophysiology, 2012; volume 5, issue 2, pages 417-424, which is incorporated herein by reference, describe a canine right atrial (RA) linear lesion model that was used to produce a complex pattern of RA activation to evaluate a mapping system for rapid, high resolution (HR) electroanatomical mapping.

U.S. Patent Application Publication 2013/0109945, whose disclosure is incorporated herein by reference, relates to the determination and/or representation of physiological information relating to a heart surface.

SUMMARY OF THE INVENTION

There is provided, in accordance with some embodiments of the present invention, a method for displaying electroanatomical information. The method includes identifying at least one multiple-activation area of a surface of a heart, at which multiple-activation area were recorded at least two different local activations during a single cardiac cycle of the heart. The multiple-activation area is displayed, on an electroanatomical map of the surface of the heart, in a manner that indicates a time difference between respective times of the two local activations.

In some embodiments, displaying the multiple-activation area includes displaying the multiple-activation area in a color that indicates the time difference.

In some embodiments, displaying the multiple-activation area includes displaying the multiple-activation area with an overlaid indicator, a property of which indicates the time difference.

In some embodiments, the property of the overlaid indicator includes a color of the overlaid indicator.

In some embodiments, the property of the overlaid indicator includes a size of the overlaid indicator.

In some embodiments, displaying the multiple-activation area includes setting a value of a display property of the multiple-activation area by applying, to the time difference, a function that maps a domain of time differences to a range of values of the display property.

In some embodiments, the function (i) is monotonic for time differences that lie between an upper limit and a lower limit, (ii) returns a first value for the lower limit, and (iii) is constant, at a second value, for differences that lie above the upper limit.

In some embodiments, the method further includes receiving from a user, via a user interface, the upper limit and the lower limit.

In some embodiments, the method further includes receiving from the user, via the user interface, the first value and the second value.

In some embodiments, the method further includes:
identifying at least one single-activation area of the surface of the heart, at which single-activation area was recorded only a single local activation during the cardiac cycle; and
displaying, on the electroanatomical map, the single-activation area in a manner that indicates a time of the single local activation.

In some embodiments,
displaying the single-activation area includes setting a color of the single-activation area by applying, to the time of the single local activation, a first function that maps a domain of times to a first range of color values, and
displaying the multiple-activation area includes setting a color of the multiple-activation area by applying, to the time difference, a second function that maps a domain of time differences to a second range of color values that is distinct from the first range.

In some embodiments, the multiple-activation area includes an area of the heart that was ablated.

There is further provided, in accordance with some embodiments of the present invention, apparatus for use with a display. The apparatus includes an electrical interface, and a processor, configured to (i) receive, via the electrical interface, one or more electrocardiogram (ECG) signals, (ii) from the ECG signals, identify at least one multiple-activation area of a surface of a heart, at which multiple-activation area were recorded at least two different local activations during a single cardiac cycle of the heart, and (iii) drive the display to display, on an electroanatomical map of the surface of the heart, the multiple-activation area in a manner that indicates a time difference between respective times of the two local activations.

There is further provided, in accordance with some embodiments of the present invention, a computer software product including a tangible non-transitory computer-readable medium in which program instructions are stored. The instructions, when read by a processor, cause the processor to (i) identify at least one multiple-activation area of a surface of a heart, at which multiple-activation area were recorded at least two different local activations during a single cardiac cycle of the heart, and (ii) drive a display to display, on an electroanatomical map of the surface of the heart, the multiple-activation area in a manner that indicates a time difference between respective times of the two local activations.

The present invention will be more fully understood from the following detailed description of embodiments thereof, taken together with the drawings, in which:

DETAILED DESCRIPTION OF EMBODIMENTS

Overview

In some procedures, the distal end of a catheter is moved along the inner or epicardial surface of a heart, and one or more electrodes at the distal end of the catheter are used to record the electrical activity of the heart. In particular, the electrodes may be used to record intracardiac ECG signals, from which the respective local activation times at various areas may be identified. Such information may be used to generate an electroanatomical map.

In some cases, some areas of the inner or epicardial surface of the heart, referred to herein as "multiple-activation areas," exhibit two or more local activations per cardiac cycle. Multiple local activations in a particular area may be indicative of the presence of a line of block in the area. Such a line of block may be pathological, or may be the intended result of an ablation procedure, referred to as a line of ablation. Moreover, the time difference between the local activations may indicate the proximity of the multiple-activation area to an edge of the line of block, or to an unintended gap in the line of ablation.

In light of the above, embodiments described herein provide methods and apparatus for displaying multiple-activation areas on an electroanatomical map, in an intuitive manner that indicates the respective time differences for the multiple-activation areas. For example, a function may be used to map the time differences to respective colors, such that the color in which a particular multiple-activation area is displayed on the map indicates the time difference for the multiple-activation area. A physician may then use the electroanatomical map to locate, with relative precision, a pathological line of block, or to identify an unintended gap in a line of ablation.

An advantage of embodiments of the present invention is that the physician need not examine the "raw" intracardiac ECG signal in order to determine the time difference between activations for a multiple-activation area. Rather, the physician may readily perceive the time difference, simply by looking at the electroanatomical map. Moreover, since the electroanatomical map typically shows all of the multiple-activation areas at once, the physician may locate pathological tissue, or an unintended gap in a line of ablation, much more quickly and/or effectively, relative to if the physician were to examine each individual intracardiac ECG signal. Hence, embodiments of the present invention may improve the diagnosis and/or treatment of the subject.

It is noted that in the context of the present application, including the claims, terms that include the word "line," such as "line of block" and "line of ablation," include within their scope any relevant type of open or closed rectilinear or curvilinear shape, of constant or varying thickness. For example, embodiments described herein may be used to identify an unintended gap in a circular line of ablation around an opening to a pulmonary vein, or a straight or curved line of ablation in any area of the heart.

System Description

Figure 1:
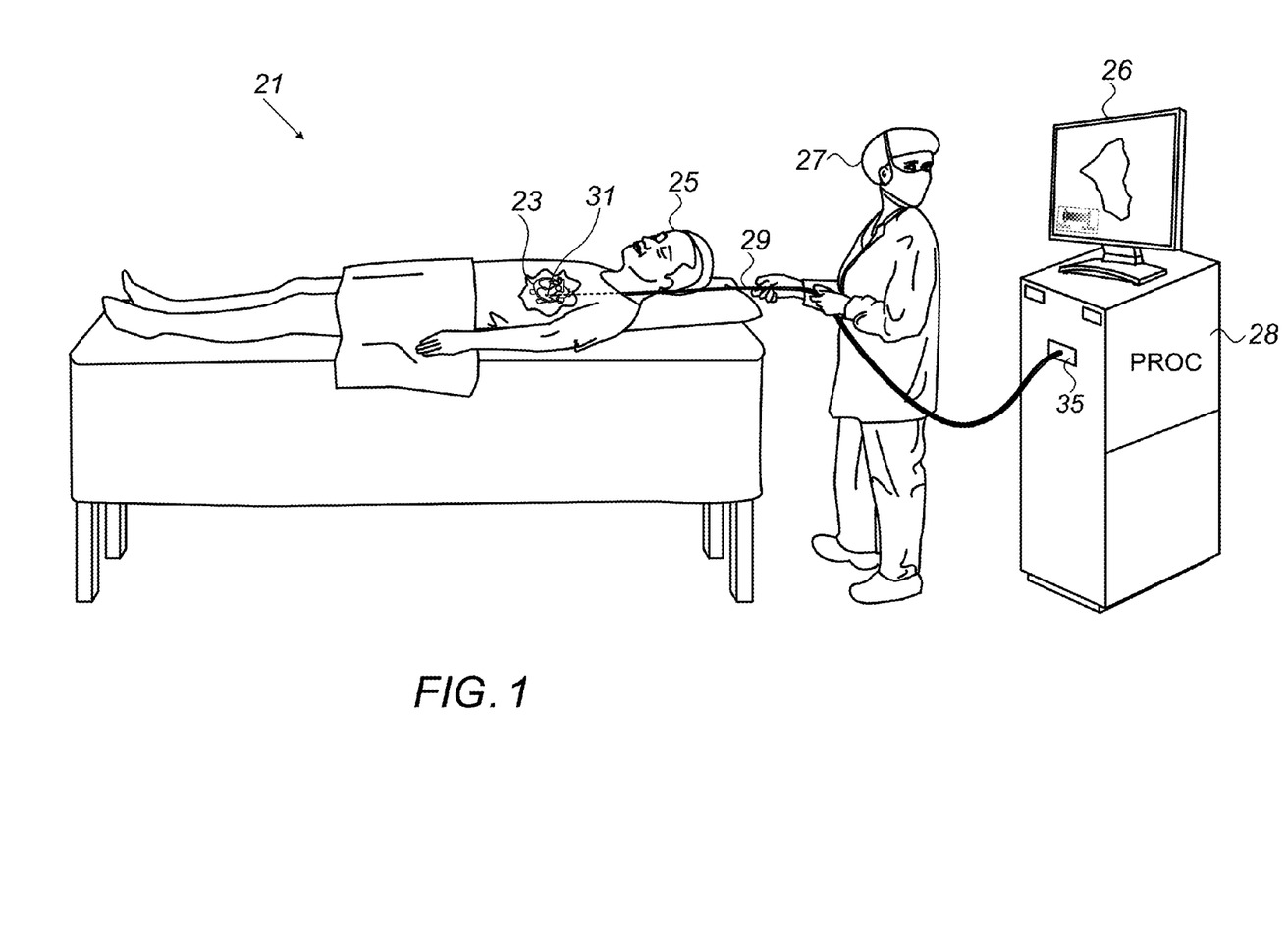
FIG. 1 is a schematic illustration of a system for generating an electroanatomical map of an inner or epicardial surface of a heart, in accordance with some embodiments of the present invention.

Reference is initially made to FIG. 1, which is a schematic illustration of a system 21 for generating an electroanatomical map of an inner or epicardial surface of a heart 23 of a subject 25, in accordance with some embodiments of the present invention. In generating the electroanatomical map, methods disclosed in U.S. Pat. Nos. 6,226,542, 6,301,496, and 6,892,091, whose disclosures are herein incorporated by reference, may be used. One commercial product embodying elements of system 21 is the CARTO® 3 System, available from Biosense Webster, Inc., 3333 Diamond Canyon Road, Diamond Bar, Calif. 91765. This system may be modified by those skilled in the art to embody the principles of embodiments described herein.

FIG. 1 shows a physician 27 holding a catheter 29, a distal end 31 of which is disposed within heart 23 of subject 25. Physician 27 moves distal end 31 of catheter 29 along the inner or epicardial surface of the heart, and one or more electrodes at the distal end of the catheter are used to record intracardiac ECG signals, as described above. A processor (PROC) 28 receives the ECG signals via an electrical interface 35. By analyzing the ECG signals, processor 28 identifies any recorded local activations, and further measures the respective local activation times of the local activations, or at least the respective differences between any multiple local activations. In response to the measured local activation times and/or the time differences, processor 28 generates an electroanatomical map, and drives a display 26 to display the map, as described in detail below.

In general, processor 28 may be embodied as a single processor, or a cooperatively networked or clustered set of processors. Processor 28 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the computer in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Figure 2:
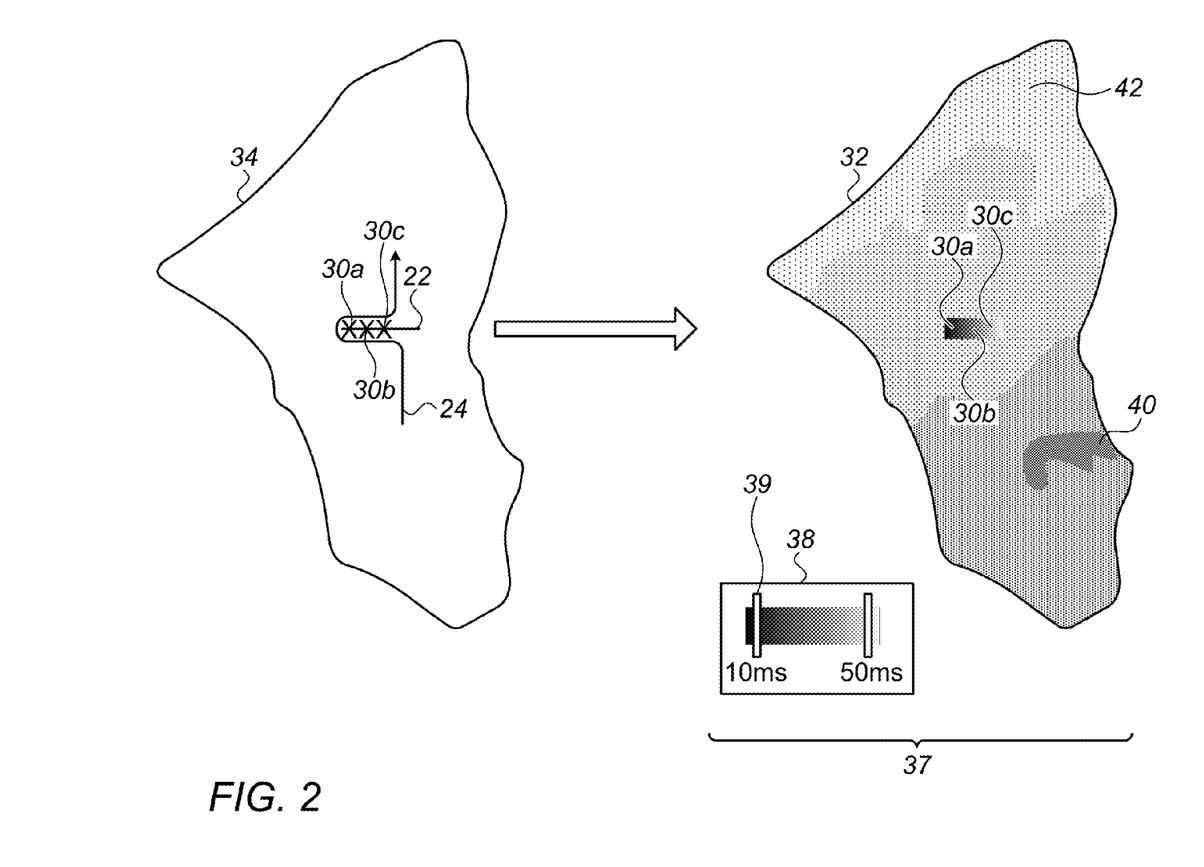
FIGS. 2-3 are schematic illustrations of visual output, displayed in accordance with some embodiments of the present invention.

Reference is now additionally made to FIG. 2, which is a schematic illustration of visual output 37, which is displayed on display 26 in accordance with some embodiments of the present invention. Visual output 37 includes an electroanatomical map 32 of an inner surface 34 of a heart (e.g., a portion of the left-ventricular or right-ventricular myocardium of the heart), which is generated by processor 28 in response to the local activation times of the recorded local activations.

The left side of FIG. 2 shows the anatomical scenario that leads to the display of map 32 as shown. In this scenario, an electrical wavefront 24 propagates along surface 34, as indicated by the arrow. Upon reaching the "near" side of a line of block 22, wavefront 24 circumvents the line of block, and continues along its previous trajectory at the "far" side of the line of block. As a result of the circumvention of line of block 22, multiple local activation times are measured in the vicinity of the line of block. For example, FIG. 2 depicts, via a plurality of "x" symbols, the measurement of local activation times at areas 30a, 30b, and 30c that lie along the line of block. At each of these areas, at least two local activation times are measured per cardiac cycle: a first local activation time corresponding to the passing of wavefront 24 through the near side of the area, and a second local activation time corresponding to the passing of wavefront 24 through the far side of the area. For example, the measured local activation times might be as follows:

Area 30a: 300 ms and 310 ms
Area 30b: 290 ms and 320 ms
Area 30c: 280 ms and 330 ms Areas such as areas 30a, 30b, and 30c are referred to herein as "multiple-activation areas." On the other hand, areas in which only a single local activation is recorded per cardiac cycle are referred to herein as "single-activation areas." (As further described below, areas at which multiple local activations are recorded, but these local activations occur relatively close together in time, may be treated as single-activation areas.) The difference between the local activation times at a multiple-activation area is a function of the propagation time needed for wavefront 24 to circumvent the line of block, and is therefore a function of the proximity of the multiple-activation area to the edge of the line of block. Thus, per the example above, the difference between the local activation times is 50 ms for area 30c, but only 10 ms for area 30a, since area 30a is closer to the edge of the line of block.

Based on the measured local activation times, processor 28 identifies areas 30a, 30b, and 30c as multiple-activation areas. Processor 28 then drives display 26 to display, on electroanatomical map 32, each of the multiple-activation areas in a manner that indicates the time difference between the two local activation times measured at the area. For example, FIG. 2 shows each of areas 30a, 30b, and 30c displayed in a color that indicates the time difference between the two local activation times measured at the area. In particular, area 30a, at which a relatively small time difference was measured, is shown in a darker color, while area 30c, at which a larger time difference was measured, is shown in a lighter color. Area 30b is shown in an intermediate color. (It is noted that in the context of the present application, including the claims, black is considered to be a color.)

Typically, to display the multiple-activation area such as to indicate the time difference between the two local activation times, the processor sets a value of a display property of the multiple-activation area by applying, to the time difference, a function that maps a domain of time differences to a range of values of the display property. For example, as noted above, FIG. 2 depicts an embodiment in which the modified display property is the display color; hence, the processor applies a function that maps a domain of time differences delta-T ($\Delta T$) to a range of color values. Such a range may be expressed in terms of any relevant color space.

Typically, the function that is used for displaying the multiple-activation areas (i) is monotonic (e.g., strictly monotonic) for time differences that lie between an upper limit and a lower limit, (ii) returns a first value for the lower limit, and (iii) is constant, at a second value, for differences that lie above the upper limit. For example, in the RGBA color space, and assuming a lower limit of 10 ms and an upper limit of 50 ms, the function may take the following form:

$$C2\_R = C2\_G = C2\_B = (\max(\min(\Delta T, 50), 10) - 10)/40,$$

$$C2\_A = 1,$$

where C2_R, C2_G, and C2_B are, respectively, the red (R), green (G), and blue (B) components of the color C2 in which the multiple-activation area is displayed, and C2_A is the opacity of the color. (Hence, this function maps the domain of time differences to the color range between black, represented by the RGBA vector (0,0,0,1), and white, represented by (1,1,1,1).) For each of the color components, this function (i) is strictly monotonically (linearly) increasing, from 0 to 1 for $\Delta T$ values between 10 ms and 50 ms, (ii) returns 0 for $\Delta T$ values less than or equal to 10 ms, and (iii) returns 1 for $\Delta T$ values greater than or equal to 50 ms.

It is noted that the scope of the present invention includes setting any relevant display property to indicate the time difference between the local activation times. For example, in some embodiments, alternatively or additionally to setting the color of the multiple-activation area, the multiple-activation area may be displayed with an overlaid indicator (e.g., a "+," "x," or "*" symbol), a property of which indicates the time difference between the two local activation times. For example, the color or size of the overlaid indicator may indicate the time difference. In such embodiments, a function may be used to map the relevant domain of time differences to the relevant range of values for the color or size of the indicator, analogously to that which was described above. For example, for embodiments in which the time differences are mapped to different indicator sizes, the function may, for example, take the form $$S = (\max(\min(\Delta T, 50), 10) - 10)/4,$$

where S is the size, in pixels, of the indicator. Such a function returns a size of zero pixels for $\Delta T$ values equal to or less than 10 ms, a size of 10 pixels for $\Delta T$ values equal to or greater than 50 ms, and a size that varies linearly from zero to 10 pixels for $\Delta T$ values between 10 ms and 50 ms.

In the above examples, the mapping function is linearly increasing between the upper and lower time-difference limits. In other embodiments, the mapping function may be exponential or logarithmic, or may take any other suitable form.

As depicted in FIG. 2, in some embodiments, the upper and lower limits of the domain for the monotonically varying portion of the function, and/or the corresponding values of the range, are received from a user (e.g., the physician) via a user interface 38, which is included in visual output 37. For example, FIG. 2 depicts user interface 38 taking the form of a color bar. By sliding two sliders 39 along the color bar, the user is able to choose the upper and lower limits, as well as the colors in which these limits are displayed.

In other embodiments, the upper and lower limits are not received from a user, but rather, are calculated based on the distribution of $\Delta T$. In yet other embodiments, the upper and lower limits are preset, constant values.

Typically, the lower limit of the domain is also the cutoff for identifying multiple-activation areas. For example, if the lower limit is 10 ms, areas having time differences of less than 10 ms may be treated as single-activation areas, despite these areas exhibiting multiple activations. In other embodiments, however, the cutoff may be different from the lower limit. For example, user interface 38 may allow the user to separately input a cutoff. Thus, for example, if the user inputs a cutoff of 5 ms, a lower limit of 10 ms, and an upper limit of 50 ms, assuming a black color for the lower limit and a white color for the upper limit:

(i) areas having a $\Delta T$ value that is less than 5 ms will be classified as single-activation areas;

(ii) areas having a $\Delta T$ value between 5 ms and 10 ms will be displayed in black;

(iii) areas having $\Delta T$ values between 10 ms and 50 ms will be displayed in varying shades of gray; and (iv) areas having $\Delta T$ values that are 50 ms or greater will be displayed in white.

Some multiple-activation areas may exhibit more than two local activation times. In some embodiments, for such areas, the processor attempts to identify one or more of the local activation times as outliers, by, for example, comparing the local activation times to those of nearby areas. By disregarding any identified outliers, the number of local activation times is reduced. If more than two local activation times remain even after disregarding the outliers, the processor may, for example, calculate ΔT as the difference between the first and last local activation times. In other embodiments, the processor does not attempt to identify any outliers, but rather, simply calculates ΔT as the difference between the first and last local activation times, or uses any other suitable method to choose the "primary" two local activation times.

In some embodiments, the processor ignores any portions of the intracardiac ECG that were recorded during portions of the cardiac cycle in which electrical noise is known to be relatively high. This may reduce the number of spurious local activations that are identified.

Typically, processor 28 further identifies at least one single-activation area, and displays, on map 32, the single-activation area in a manner that indicates the single local activation time of the single-activation area. For example, in FIG. 2, single-activation areas are identified for the majority of surface 34, and these single-activation areas are displayed on the map in different colors (indicated in FIG. 2 by different dot-pattern densities), which indicate the different respective local activation times of the areas.

Typically, to set the display-property values for the single-activation areas, the processor applies a function that maps a domain of local activation times to a range of display-property values. For example, the processor may apply a function that maps a domain of local activation times T to a range of color values C1, which is distinct from the range of color values C2 in which the multiple-activation areas are displayed. For example, C2 may range between black and white, with C1 ranging across other colors such as blue, red, violet, etc. The use of distinct color-value ranges allows the physician to easily distinguish between multiple-activation areas and single-activation areas.

In some embodiments, the upper and lower local-activation-time limits, and/or the range of display-property values for the single-activation areas, is received via user interface 38. For example, the user interface may include a separate color bar, and accompanying sliders, for setting the relevant values.

For embodiments in which the display color is set to indicate the relevant time differences (for multiple-activation areas) and/or the relevant local activation times (for single-activation areas), color interpolation may be used to assign color values to certain areas at which ECG recordings were not performed. Such interpolation, which may be performed in accordance with any relevant technique known in the art, typically gives the electroanatomical map a smooth appearance, thus allowing the electroanatomical map to be more readily interpreted. For example, if a first area is assigned a color value of (0,0,0,1), and a nearby, second area is assigned a color value of (20,20,20,1), areas that lie between the first and second areas may be assigned color values that increase (e.g., linearly) from (0,0,0,1) to (20,20,20,1).

The showing of both the single-activation areas and multiple-activation areas as described herein, particularly together on the map at the same time, helps the physician diagnose the subject's condition and/or decide upon an appropriate course of treatment. The respective display-property values of the single-activation areas indicate to the physician the direction of electrical propagation, while the respective display-property values of the multiple-activation areas additionally indicate the location of any lines of block. Thus, for example, given the display shown in FIG. 2, the physician may ascertain, based on the colors in which the single-activation areas are displayed, that the wavefront of electrical activity propagates outward from an area 40 of surface 34, in all directions, including toward an area 42 of the surface. The colors in which the multiple-activation areas are displayed further indicate that a line of block is located along the route from area 40 to area 42, the edge of the line of block being at area 30a.

Notwithstanding the above, in some embodiments, only the double-activation areas are displayed with indicative display-property values. Thus, for example, the double-activation areas may be displayed in the black-white color range, while the single-activation areas are displayed in a single color.

Typically, display 26 includes a legend that shows the mapping that was used to display the multiple-activation areas, and/or the mapping that was used to display the single-activation areas. For example, user interface 38 may include such a legend, in the form of the color bars described above.

Figure 3:
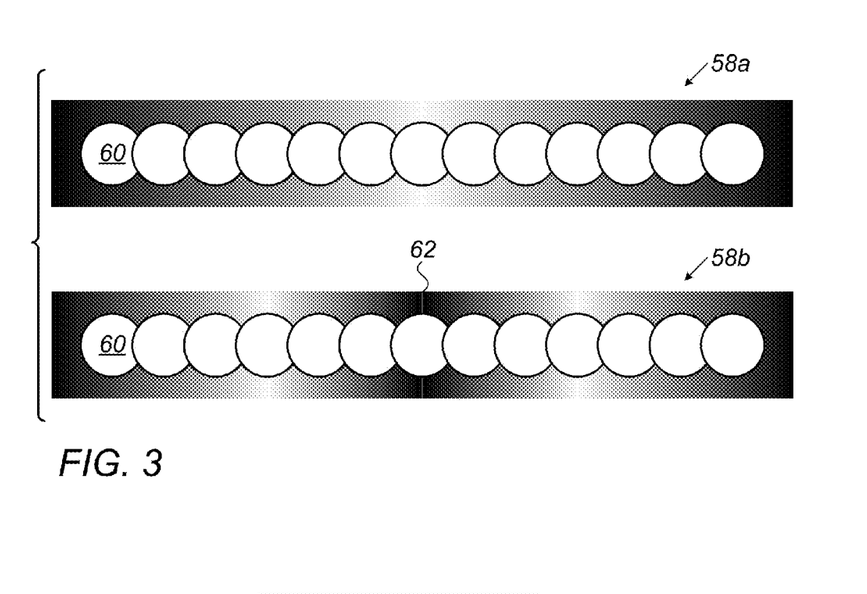

Reference is now made to FIG. 3, which is a schematic illustration of visual output 58a and 58b, displayed in accordance with some embodiments of the present invention.

As noted above, embodiments described herein may be used to locate a pathological line of block. Analogously, embodiments described herein may be used to identify an unintended gap in a line of ablation, which is a line of electrically non-conductive tissue created by a physician during an ablation procedure, typically in order to terminate or alter an arrhythmia of the subject.

In both visual output 58a and visual output 58b, a plurality of markers 60, superimposed on map 32, mark the areas that the physician attempted to ablate. Visual output 58a corresponds to a scenario in which the line of ablation is continuous, as intended. In such a scenario, the varying colors of the multiple-activation areas provide intuitive, visual feedback to the physician that the ablation was successful. Visual output 58b, on the other hand, corresponds to a scenario in which the line of ablation has an unintended gap 62. In such a scenario, the varying colors of the multiple-activation areas provide intuitive, visual feedback to the physician that the ablation was not entirely successful. In response thereto, the physician may reablate the area at gap 62.

Figure 4:
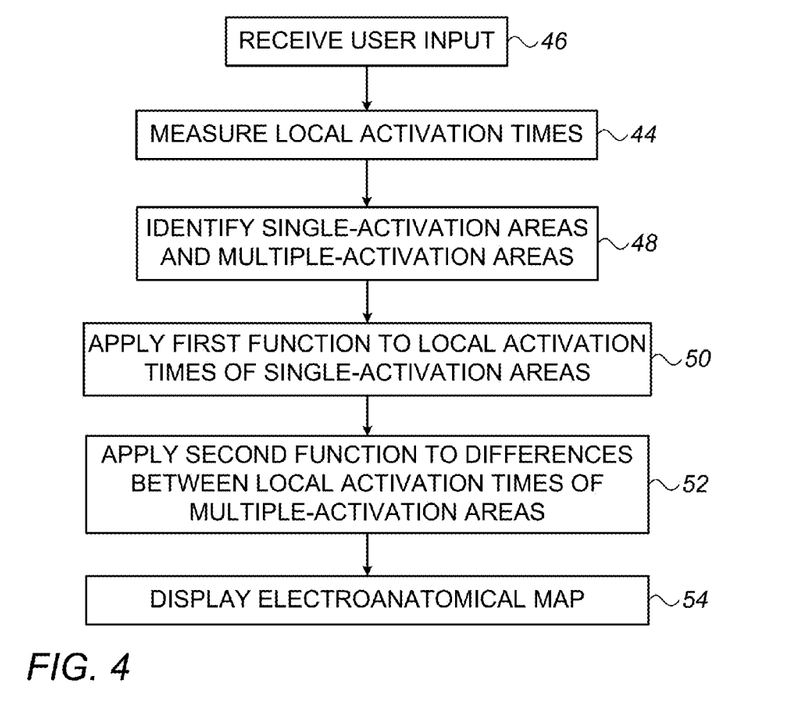
FIG. 4 is a flow diagram for a method for displaying an electroanatomical map of an inner or epicardial surface of a heart, in accordance with some embodiments of the present invention.

Reference is now made to FIG. 4, which is a flow diagram for a method for displaying an electroanatomical map of an inner or epicardial surface of a heart, in accordance with some embodiments of the present invention.

First, via user interface 38 (FIG. 2), user input is received, at an input-receiving step 46. As described above, such input includes the information that is used to map local-activation-time differences to display-property values for the multiple-activation areas, and/or the information that is used to map local activation times to display-property values for the single-activation areas. Subsequently, at a measuring step 44, the local activation times for a plurality of areas of the surface are measured, as described above. (In some embodiments, input-receiving step 46 is performed subsequently to measuring step 44.)

Subsequently, at an identifying step 48, each of the areas of the surface is identified as being either a single-activation area or a multiple-activation area. A single-activation area is any area for which either (i) only one local activation time was measured, or (ii) the difference between local activation times is less than a cutoff. As described above, the cutoff is typically the lower time-difference limit for the multiple-activation-area mapping. Thus, for example, if the user inputs a lower limit of 10 ms, any area for which the difference between local activation times is less than 10 ms will be classified as a single-activation area.

Subsequently, at a first-function-applying step 50, a first function, which is based on the received user input, is used to map the local activation times of the single-activation areas to respective display-property values. Similarly, at a second-function-applying step 52, a second function, which is also based on the received user input, is used to map the differences between local activation times of the multiple-activation areas to respective display-property values. The electroanatomical map is then displayed, at a displaying step 54, with the display-property values calculated in steps 50 and 52. The physician may then use the electroanatomical map to diagnose the subject.

It is noted that apparatus and methods described herein may be practiced with both static electroanatomical maps, which do not change from one heartbeat to the next, and dynamic electroanatomical maps. Such dynamic electroanatomical maps may be used, for example, to visualize changes in the pattern of electrical propagation from one heartbeat to the next, in order to better diagnose and/or treat certain types of arrhythmias.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
contacting a distal end of a catheter along a surface of a heart, the distal end of the catheter having one or more electrodes configured to sense intracardiac ECG signals,
receiving the ECG signals in a processor operatively connected to the electrodes by an interface;
analyzing the ECG signals in the processor to identify at least one multiple-activation area of the surface of the heart, wherein the at least one multiple-activation area of the surface of the heart occurs where at least two different local activations of the same area are received during a single cardiac cycle of the heart;
generating an electroanatomical map of the surface of the heart in the processor and displaying the electroanatomical map of the surface of the heart on a display device; and
displaying, on the electroanatomical map of the surface of the heart, the multiple-activation area in a manner that indicates a time difference between respective times of the two local activations.

2. The method according to claim 1, wherein displaying the multiple-activation area comprises displaying the multiple-activation area in a color that indicates the time difference.

3. The method according to claim 1, wherein displaying the multiple-activation area comprises displaying the multiple-activation area with an overlaid indicator, a property of which indicates the time difference.

4. The method according to claim 1, wherein displaying the multiple-activation area comprises setting a value of a display property of the multiple-activation area by applying, to the time difference, a function that maps a domain of time differences to a range of values of the display property.

5. The method according to claim 4, wherein the function (i) is monotonic for time differences that lie between an upper limit and a lower limit, (ii) returns a first value for the lower limit, and (iii) is constant, at a second value, for differences that lie above the upper limit.

6. The method according to claim 5, further comprising receiving from a user, via a user interface, the upper limit and the lower limit.

7. The method according to claim 6, further comprising receiving from the user, via the user interface, the first value and the second value.

8. The method according to claim 1, further comprising:
identifying at least one single-activation area of the surface of the heart, wherein said single-activation area occurs when only a single local activation occurs during the cardiac cycle; and
displaying, on the electroanatomical map, the single-activation area in a manner that indicates a time of the single local activation.

9. The method according to claim 8,
wherein displaying the single-activation area comprises setting a color of the single-activation area by applying, to the time of the single local activation, a first function that maps a domain of times to a first range of color values, and
wherein displaying the multiple-activation area comprises setting a color of the multiple-activation area by applying, to the time difference, a second function that maps a domain of time differences to a second range of color values that is distinct from the first range.

10. The method according to claim 1, wherein the multiple-activation area includes an area of the heart that was ablated.

11. Apparatus, comprising:
A probe having one or more electrodes along its distal end, the electrodes configured to record intracardiac ECG signals;
an electrical interface operatively connected to the electrodes;
a display; and
a processor operatively connected to the electrical interface, the processor being configured to:
receive, via the electrical interface, one or more ECG signals, and from the ECG signals, identify at least one multiple-activation area of a surface of a heart, wherein the at least one multiple-activation area occurs when at least two different local activations of the same area are received during a single cardiac cycle of the heart,
generate an electroanatomical map of the surface of the heart, and
drive the display to display, on the map of the surface of the heart, the multiple-activation area in a manner that indicates a time difference between respective times of the two local activations.

12. The apparatus according to claim 11, wherein the processor is configured to drive the display to display the multiple-activation area in a color that indicates the time difference.

13. The apparatus according to claim 11, wherein the processor is configured to drive the display to display the multiple-activation area with an overlaid indicator, a property of which indicates the time difference.

14. The apparatus according to claim 13, wherein the property of the overlaid indicator includes a color of the overlaid indicator.

15. The apparatus according to claim 13, wherein the property of the overlaid indicator includes a size of the overlaid indicator.

16. The apparatus according to claim 11, wherein the processor is configured to set a value of a display property of the multiple-activation area by applying, to the time difference, a function that maps a domain of time differences to a range of values of the display property.

17. The apparatus according to claim 16, wherein the function (i) is monotonic for time differences that lie between an upper limit and a lower limit, (ii) returns a first value for the lower limit, and (iii) is constant, at a second value, for differences that lie above the upper limit.

18. The apparatus according to claim 17, wherein the processor is further configured to receive from a user, via a user interface, the upper limit and the lower limit.

19. The apparatus according to claim 11, wherein the processor is further configured to:
from the ECG signals, identify at least one single-activation area of the surface of the heart, wherein the at which single-activation area occurs when only a single local activation was recorded during the cardiac cycle, and
drive the display to display, on the electroanatomical map, the single-activation area in a manner that indicates a time of the single local activation.

20. The apparatus according to claim 19, wherein the processor is configured to:
set a color of the single-activation area by applying, to the time of the single local activation, a first function that maps a domain of times to a first range of color values, and
set a color of the multiple-activation area by applying, to the time difference, a second function that maps a domain of time differences to a second range of color values that is distinct from the first range.

21. A computer software product comprising a tangible non-transitory computer-readable medium in which program instructions are stored, which instructions, when read by a processor, cause the processor to:
receive ECG signals from an electrode operatively connected to the processor by an interface, the configured to be in contact with a surface of the heart;
analyze the ECG signals in the processor to identify at least one multiple-activation area of a surface of the heart, the at least one multiple-activation area of the surface occurs when at least two different local activations of the same area are received during a single cardiac cycle of the heart,
generate an electroanatomical map, and
drive a display to display, on the electroanatomical map of the surface of the heart, the multiple-activation area in a manner that indicates a time difference between respective times of the two local activations.

* * * * *